(12) United States Patent
Whitcup et al.

(10) Patent No.: US 11,179,388 B2
(45) Date of Patent: Nov. 23, 2021

(54) TOPICAL COMPOSITION FOR TREATING ROSACEA AND A METHOD FOR TREATING ROSACEA WITH THE SAME

(71) Applicants: Scott Whitcup, Irvine, CA (US); Rong Yang, Mission Viejo, CA (US); Jinsong Ni, Irvine, CA (US)

(72) Inventors: Scott Whitcup, Irvine, CA (US); Rong Yang, Mission Viejo, CA (US); Jinsong Ni, Irvine, CA (US)

(73) Assignee: ADS THERAPEUTICS LLC, Irvine, CA (US)

( * ) Notice: Subject to any disclaimer, the term of this patent is extended or adjusted under 35 U.S.C. 154(b) by 0 days.

(21) Appl. No.: 16/616,444

(22) PCT Filed: May 25, 2018

(86) PCT No.: PCT/US2018/034583
§ 371 (c)(1),
(2) Date: Nov. 22, 2019

(87) PCT Pub. No.: WO2018/218116
PCT Pub. Date: Nov. 29, 2018

(65) Prior Publication Data
US 2020/0121675 A1 Apr. 23, 2020

Related U.S. Application Data

(60) Provisional application No. 62/511,929, filed on May 26, 2017.

(51) Int. Cl.
| *A61K 31/496* | (2006.01) |
| *A61K 31/4164* | (2006.01) |
| *A61K 31/135* | (2006.01) |
| *A61P 17/00* | (2006.01) |
| *A61K 31/44* | (2006.01) |
| *A61K 9/00* | (2006.01) |

(52) U.S. Cl.
CPC .......... *A61K 31/496* (2013.01); *A61K 9/0014* (2013.01); *A61K 31/135* (2013.01); *A61K 31/4164* (2013.01); *A61K 31/44* (2013.01); *A61P 17/00* (2018.01)

(58) Field of Classification Search
CPC .. A61K 31/496; A61K 9/0014; A61K 31/135; A61K 31/4164; A61K 31/44; A61K 9/06; A61K 31/4174; A61K 31/498; A61P 17/00
See application file for complete search history.

(56) References Cited

U.S. PATENT DOCUMENTS

| 2013/0079379 A1 | 3/2013 | Shanler et al. |
| 2014/0031310 A1 | 1/2014 | Maki et al. |
| 2016/0257693 A1 | 9/2016 | Enlow et al. |
| 2019/0388407 A1* | 12/2019 | Tang-Liu ............... A61K 31/47 |

FOREIGN PATENT DOCUMENTS

| WO | 2017053807 A2 | 3/2017 |
| WO | 2017062694 A1 | 4/2017 |
| WO | 2018148653 A1 | 8/2018 |

OTHER PUBLICATIONS

Kimmick et al., "Cardio-Oncology: The Clinical Overlap of Cancer and Heart Disease", Springer, Apr. 2017—Medical—319 pages.
Wikipedia, "Rossacea", Feb. 16, 2017, retrieved on Aug. 2, 2018 from https://en.wikipedia.org/w/index.php?title=Rosacea&oldid=765720457.
Woo et al., "Rosacea: Molecular Mechanisms and Management of a Chronic Cutaneous Inflammatory Condition", Int. J. Mol. Sci. 2016, 17, 1562, Sep. 15, 2016.
Wollin et al., "Mode of action of nintedanib in the treatment of idiopathic pulmonary fibrosis", Eur Respir J, 2015; 45:1434-1445, Mar. 5, 2015.
Nijnik et al., "The role of the Src family kinase Lyn in the immunomodulatory activities of cathelicidin peptide LL-37 on monocytic cells", J Leukoc Biol. Apr. 2012; 91(4).
Wikipedia, "Brimonidine", Dec. 14, 2016, retrieved on Aug. 2, 2018 from https://en/wikipedia.org/w/index.php?title=Brimonidine&oldid=754745762.

* cited by examiner

*Primary Examiner* — Jason Deck
(74) *Attorney, Agent, or Firm* — SZDC Law P.C.

(57) ABSTRACT

A composition for use in the treatment of rosacea includes a multi-kinase inhibitor that inhibits both a Vascular Endothelial Growth Factor Receptor and a Fibroblast Growth Factor Receptor. A method for treating rosacea for a patient includes inhibiting a Vascular Endothelial Growth Factor Receptor of the patient; and inhibiting a Fibroblast Growth Factor Receptor of the patient.

5 Claims, 1 Drawing Sheet

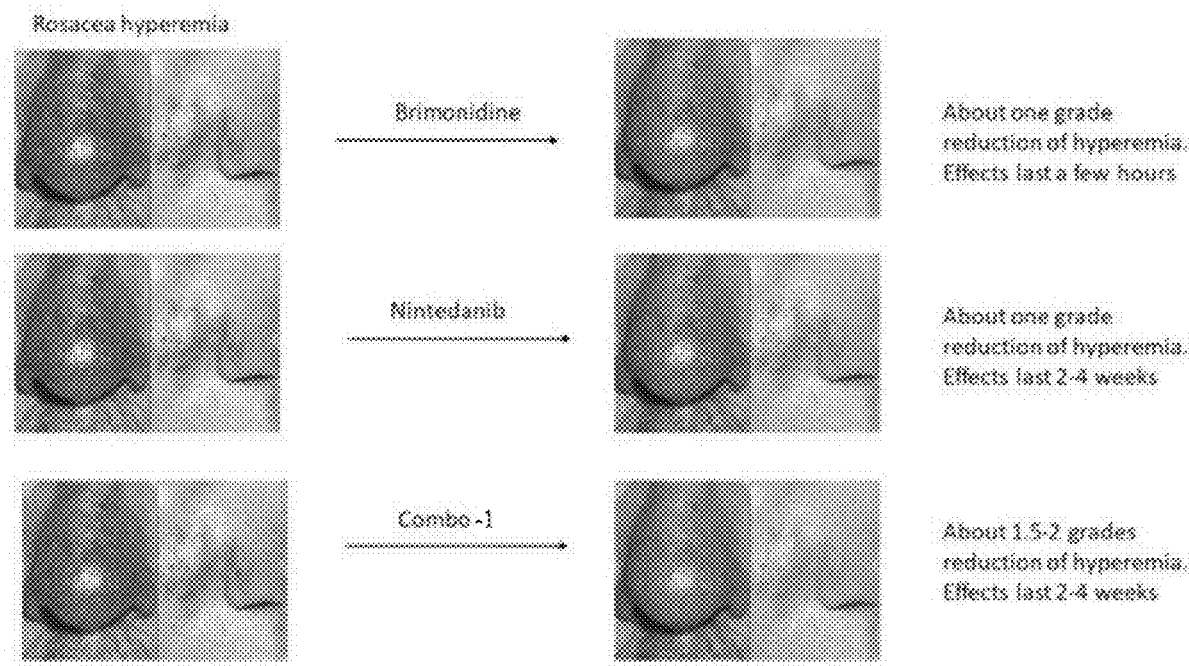

TOPICAL COMPOSITION FOR TREATING ROSACEA AND A METHOD FOR TREATING ROSACEA WITH THE SAME

This application is the National Stage Application of PCT/US2018/034583, filed on May 25, 2018, which claims priority to U.S. Provisional Patent Application No.: 62/511,929, filed on May 26, 2017, which is incorporated by reference for all purposes as if fully set forth herein.

FIELD OF THE INVENTION

The present invention relates to a composition for treating rosacea and a method for treating rosacea with the same, more specifically, a topical composition including a multi-kinase inhibitor (MKI) for treating rosacea and a method for treating rosacea with the same.

BACKGROUND OF THE INVENTION

Rosacea Disease and Subtypes

Rosacea is a common chronic skin disease usually involving abnormal immune and neurovascular regulations. It affects about 10% of the population and the prevalence is highest among fair-skinned individuals. Most of the skin lesions of rosacea occur on the central face, such as the cheeks, forehead, chin, and nose. There are four major subtypes of the disease.

Subtype 1—erythematotelangiectatic rosacea: characterized by flushing and persistent redness; subtype 2—papulopustular rosacea: characterized by persistent redness with transient papules and pustules; subtype 3—phymatous rosacea: characterized by skin thickening, often resulting in an enlargement of the nose from excess tissue; subtype 4—ocular rosacea: characterized by ocular manifestations such as dry eye, tearing and burning, swollen eyelids, recurrent hordeolum and potential vision loss from corneal damage.

Several subtypes are often manifested in one patient at the same time, and the clinical manifestations of rosacea are more diverse. Rosacea presents with primary clinical cutaneous signs including transient erythema (flushing), persistent erythema, telangiectasia, papules, pustules, skin fibrosis and glandular hyperplasia. Associated secondary symptoms like burning, stinging or pain can also occur.

Pathogenesis and Molecular Mechanism

Like the phenotype of the disease, the causes of rosacea are also very complex and not completely understood. Genetics studies have revealed about 47% genetic contribution (Holmes et al. 2016). Several chromosomal loci such as HLA-DRA are linked to higher risk of the disease. Many external inducers such as ultraviolet radiation, demodex colonization and heat are also identified as rosacea induction factors.

The pathogenesis of rosacea is extremely complex. Immune abnormality has been identified as a key pathogenic factor of the disease and both innate and adaptive immunity are implicated. For example, TLR-2 and LL-37/cathelicidin have major roles in the disease. The tyrosine kinase Lyn may have a role downstream in LL-37 mediated immunoregulation. Another major pathogenic factor of rosacea is neurovascular dysregulation. Many neuromodulators are abnormally regulated in the disease.

Current Management of Rosacea

Although no effective cure for rosacea exists, several treatments are currently used to manage the disease. They are designed to suppress the inflammatory lesions, erythema, and to a lesser extent, the telangiectasia involved with rosacea.

Topical α-adrenergic receptor agonists such as brimonidine and oxymetazoline can reduce persistent facial erythema in rosacea by vasoconstricting dermal blood vessels and counter the vasodilation in rosacea. Nonselective beta-blockers also have effects by similar mechanism. Botulinum toxin has been reported to reduce erythema possibly through neuromuscular junction modulation. Topical sodium sulfacetamide can reduce rosacea inflammatory lesion and erythema. Topical metronidazole is effective in treating rosacea because of its ability to decrease reactive oxygen species (ROS) generation. Topical azelaic acid reduces rosacea lesion by decreasing the expression of kallikrein 5 and cathelicidin, two important components of the inflammatory cascade in rosacea. Topical ivermectin works through multiple mechanisms including anti-inflammation and anti-demodex mites. Topical retinoids may be effective in decreasing rosacea symptoms by reversing the contribution of ultraviolet radiation to rosacea's manifestations, and down-regulation of Toll-like receptor 2 (TLR-2). Topical calcineurin inhibitors are hypothesized to be beneficial in reducing rosacea symptoms because of their ability to inhibit T-cell activation, thereby preventing the release of proinflammatory cytokine. Other topical treatments include permethrin, praziquantel and cyclosporine A (for ocular rosacea). Systemic medications such as tetracyclines and isotretinoin are also used to treat rosacea by modulating immune targets.

While current therapeutics target inflammatory pathways, new therapeutics that inhibit neural and vascular components of disease are needed for improved long-term control of rosacea and for combination and individualized treatments.

SUMMARY OF THE INVENTION

In one embodiment, the present invention provides a composition for use in the treatment of rosacea. The composition includes a multi-kinase inhibitor that inhibits both a Vascular Endothelial Growth Factor Receptor (VEGFR) and a Fibroblast Growth Factor Receptor (FGFR).

In another embodiment, the Vascular Endothelial Growth Factor Receptor is Vascular Endothelial Growth Factor Receptor 1, 2, or 3, and the Fibroblast Growth Factor Receptor is Fibroblast Growth Factor Receptor 2.

In another embodiment, the multi-kinase inhibitor is nintedanib, regorafenib, or a pharmaceutically acceptable salt thereof In another embodiment, the composition further includes an adrenergic receptor agonist.

In another embodiment, the adrenergic receptor agonist is an α1 adrenergic receptor agonist or an α2 adrenergic receptor agonist.

In another embodiment, the α1 adrenergic agonist is selected from the group consisting of oxymetazoline, naphazoline, tetrahydrozoline, methoxamine, phenylephrine, xylometazoline, and oxedrine; and the α1 adrenergic agonist is preferably oxymetazoline.

In another embodiment, the α2 adrenergic agonist is selected from the group consisting of brimonidine, apraclonidine, mivaZerol, clonidine, alpha methyl dopa, guanfacine, dexemeditomidine, (+)-(S)-4-1-(2,3-dimethyl-phenyl)-ethyl-1,3-dihydro-imidazole-2-thione, 1-(imidazolidin-2-yl)iminolindazole, methoxamine, phenylephrine, tizanidine, xylazine, guanabenz, and amitraz; and the α2 adrenergic agonist is preferably brimonidine.

In another embodiment, the composition is a topical composition.

In another embodiment, the composition further comprises one or more selected from the group consisting of benzyl alcohol 1%; carbomer 1342; carbomer homopolymer type B; edetate disodium; medium chain triglycerides; mineral oil; purified water; sodium hydroxide; sodium thiosulfate; and sorbitan monooleate.

In another embodiment, the composition is a topical dermal composition, or an implant applied to or injected into the skin of a patient, and the topical dermal composition is preferably a cream, an ointment, a jelly, a solution, or a suspension.

In one embodiment, the present invention provides a method for treating rosacea for a patient. The method includes inhibiting a Vascular Endothelial Growth Factor Receptor of the patient; and inhibiting a Fibroblast Growth Factor Receptor of the patient.

In another embodiment, the Vascular Endothelial Growth Factor Receptor is Vascular Endothelial Growth Factor Receptor 1, 2, or 3, and the Fibroblast Growth Factor Receptor is Fibroblast Growth Factor Receptor 2.

In another embodiment, inhibiting the Vascular Endothelial Growth Factor Receptor and the Fibroblast Growth Factor Receptor comprises administering a therapeutically effective amount of nintedanib, regorafenib, or a pharmaceutically acceptable salt thereof to the patient.

In another embodiment, nintedanib or regorafenib reduces abnormal dermal blood vessel angiogenesis, leakage, density, redness, abnormal lymph angiogenesis or inflammation in the patient.

In another embodiment, nintedanib or regorafenib reduces abnormal neurovascular regulation in the patient by attenuating signals of Vascular Endothelial Growth Factor and Fibroblast Growth Factor.

In another embodiment, nintedanib inhibits Lyn kinase and attenuates LL-37 mediated inflammation in the patient.

In another embodiment, the method further includes activating an adrenergic receptor by administering a therapeutically effective amount of an adrenergic receptor agonist to the patient as a combination therapy with nintedanib or regorafenib.

In another embodiment, the adrenergic receptor agonist is an α1 adrenergic agonist selected from the group consisting of oxymetazoline, naphazoline, tetrahydrozoline, methoxamine, phenylephrine, xylometazoline, and oxedrine; and the α1 adrenergic agonist is preferably oxymetazoline.

In another embodiment, the adrenergic receptor agonist is an α2 adrenergic agonist selected from the group consisting of brimonidine, apraclonidine, mivaZerol, clonidine, alpha methyl dopa, guanfacine, dexemeditomidine, (+)-(S)-4-1-(2, 3-dimethyl-phenyl)-ethyl-1,3-dihydro-imidazole-2-thione, 1-(imidazolidin-2-yl)iminolindazole, methoxamine, phenylephrine, tizanidine, xylazine, guanabenz, and amitraz; and the α2 adrenergic agonist is preferably brimonidine.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows the treatment of erythema with 0.2% nintedanib cream, 0.3% brimonidine cream, and 0.2% nintedanib and 0.3% brimonidine cream (combo-1).

DETAILED DESCRIPTION OF THE ILLUSTRATED EMBODIMENTS

Reference will now be made in detail to embodiments of the present invention, example of which is illustrated.

The VEGFRs are tyrosine kinase receptors responsible for binding with Vascular Endothelial Growth Factor (VEGF) to initiate signal cascades that stimulate angiogenesis among other effects. VEGFR subtypes are numbered 1, 2, and 3.

The FGFRs are receptors that bind to members of the Fibroblast Growth Factor (FGF) family of proteins.

In one embodiment, the present invention provides a dual VEGFR/FGFR multi-kinase inhibitor for treating rosacea and a method for treating rosacea with the same. Preferably, the dual VEGFR/FGFR multi-kinase inhibitor inhibits Vascular Endothelial Growth Factor Receptors 1, 2, and/or 3 and Fibroblast Growth Factor Receptor 2. This method targets two rosacea pathogenic pathways not addressed by current rosacea treatments and has potential synergistic effects.

Erythema is the most common sign of rosacea and can increase in its severity over time. Increased vascular instability over time in rosacea is likely a result of repetitive insults by ROS and matrix metalloproteases (MMP), which damage and degrade vascular tissue and the supportive extracellular matrix. Whether ongoing angiogenesis contribute to the increased erythema is still unknown. It is also not clear whether telangiectasia arises from abnormal angiogenesis or whether they are pre-existing vessels that are visible due to irreparable damage to the connective tissue. VEGF is expressed by keratinocytes and lymphocytes in rosacea and is influenced by an important rosacea pathogenic factor, LL-37 (Holmes et al.). It likely contributes to angiogenesis and leucocyte chemotaxis in rosacea.

The expression of VEGF, CD31 and D2-40 was studied by immunohisto-chemistry in involved and uninvolved skin of 18 patients with erythematotelangiectatic and papulopustular rosacea (Gomaa et al). The authors observed significantly increased dermal expression of these factors in lesional versus non-lesional skin, indicating increased angiogenesis and lymphangiogenesis. Another study found signs of angiogenesis only in phymatous rosacea but not in other types of rosacea (Schwab et al.). While angiogenesis plays a role in at least a subtype of rosacea, VEGF maybe involved in most types of rosacea. UVB, an important rosacea-inducing factor, up-regulates the mRNA and protein expression of VEGF. Exposure of murine skin to UVB resulted in the production of angiogenic molecules and Fibroblast Growth Factor 2 (FGF2) from keratinocytes (Woo et al.). It is hypothesized that remodeling of the vasculature and dermal matrix by VEGF, FGF2, and MMP-1 and the production of ROS and ER stressors after UV radiation can trigger rosacea development (Woo et al.).

VEGF and FGF not only promote angiogenesis but also modulate immunity and research indicated that they may contribute to the development and progression of rosacea. Currently, no drug in the rosacea treatment arsenal specifically targets these two growth factors. The present invention uses a multi-kinase that targets VEGF and FGF signaling to treat rosacea. The multi-kinase inhibitor can reduce abnormal dermal blood vessel angiogenesis, leakage, density, and redness in the patient and reduce abnormal lymph angiogenesis and inflammation in the patient. The multi-kinase inhibitor can further attenuate the effects from Substance P mediated VEGF and FGF overexpression from mast cells and reduces abnormal neurovascular regulation in the patient. One MKI, nintedanib, can also inhibit Lyn kinase and attenuate LL-37 mediated inflammation in the patient.

Nintedanib is one example of the multi-kinase inhibitor.

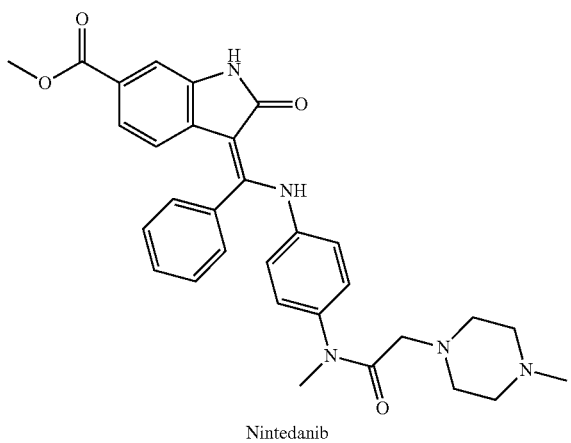

Nintedanib

The chemical name of nintedanib is (Z)-3-(1-(4-(N-((4-methyl-piperazin-1-yl)-methylcarbonyl)-N-methyl-amino)-phenylamino)-1-phenyl-methylene]-6-methoxycarbonyl-2-indolinone.

Regorafenib is another example of the multi-kinase inhibitor.

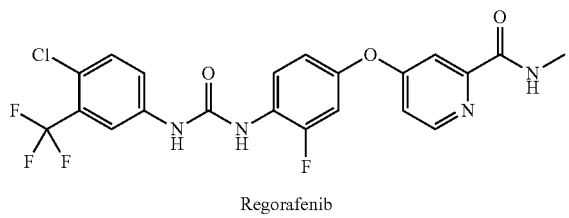 [SMILES: CNC(=O)c1cc(Oc2ccc(NC(=O)Nc3ccc(Cl)c(C(F)(F)F)c3)c(F)c2)ccn1]

Regorafenib

The chemical name of regorafenib is 4-(4-(3-(4-Chloro-3-(trifluoromethyl)phenyl)ureido)-3-fluorophenoxy)-N-methylpicolinamide.

By inhibiting both VEGF and FGF signaling, the inhibitor can improve abnormal vascularity and attenuate elevated inflammation in rosacea skin, two key pathogenic events in rosacea. Such an inhibitor can be developed into a drug as a monotherapy for rosacea or as a combination therapy with other existing rosacea drugs.

In the present invention, the term "therapeutically effective amount" as used herein means that the amount of a component (e.g., a dual VEGFR/FGFR multi-kinase inhibitor) contained in the topical composition is of sufficient quantity to achieve the intended purpose, such as, in this case, to treat rosacea. In one embodiment, the therapeutically effective amount of the dual VEGFR/FGFR multi-kinase inhibitor can be, for example, 0.001% -10.0% by weight of the total weight of the topical composition. Preferably, the therapeutically effective amount is 0.01% -5%, 0.05% -2.5%, 0.01% -1%, or 0.1% -0.5%.

In the combination therapy, the dual VEGFR/FGFR multi-kinase inhibitor can be used in combination with an adrenergic agonist, i.e., a compound that stimulates a response from the adrenergic receptors. The adrenergic agonist can be an α1 adrenergic agonist or an α2 adrenergic agonist. As used herein, "α1 adrenergic agonist" is an adrenergic agonist that is more selective for α1 adrenergic receptor than other adrenergic receptors, for example, at least 2 times more active towards α1 adrenergic receptor than other adrenergic receptors; and "α2 adrenergic agonist" is an adrenergic agonist that is more selective for α2 adrenergic receptor than other adrenergic receptors, for example, at least 2 times more active towards α2 adrenergic receptor than other adrenergic receptors.

The α1 adrenergic agonist can be selected from the group consisting of oxymetazoline, naphazoline, tetrahydrozoline, methoxamine, phenylephrine, xylometazoline, and oxedrine. Preferably, the α1 adrenergic agonist is oxymetazoline.

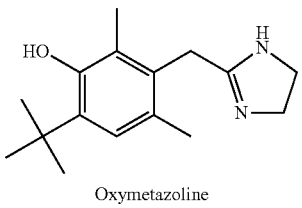 [SMILES: Cc1cc(C(C)(C)C)c(O)c(C)c1CC1=NCCN1]

Oxymetazoline

The chemical name of oxymetazoline is 6-tert-butyl-3-(4,5-dihydro-1H-imidazol-2-ylmethyl)-2,4-dimethylphenol.

The α2 adrenergic agonist can be selected from the group consisting of brimonidine, apraclonidine, mivaZerol, clonidine, alpha methyl dopa, guanfacine, dexemeditomidine, (+)-(S)-4-1-(2,3-dimethyl-phenyl)-ethyl-1,3-dihydro-imidazole-2-thione, 1-(imidazolidin-2-yl)iminolindazole, methoxamine, phenylephrine, tizanidine, xylazine, guanabenz, and amitraz. Preferably, the α2 adrenergic agonist is brimonidine.

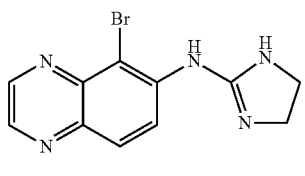

Brimonidine

The chemical name of brimonidine is (5-bromoquinoxalin-6-yl)-(4,5-dihydro-1H-imidazol-2-yl)-amine.

The dual VEGFR/FGFR multi-kinase inhibitor can be used as the form of a pharmaceutically acceptable salt, in which the salt is preferably acid addition salt formed by pharmaceutically acceptable free acids. The acid addition salt can be obtained from inorganic acids such as hydrochloric acid, nitric acid, phosphoric acid, sulfuric acid, hydrobromic acid, hydroiodic acid, nitrous acid and phosphorous acid, or non-toxic organic acids such as aliphatic mono/dicarboxylate, phenyl-substituted alkanoate, hydroxy alkanoate, alkandioate, aromatic acids and aliphatic/aromatic sulfonic acids.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions, suspensions, creams, ointments, gels, gel-forming liquid, suspension containing liposomes or micelles, spray formulation.

The topical composition of the present invention can be a topical dermal composition or an implant applied to or injected into the skin of a patient. Preferably, the topical dermal composition is a cream, an ointment, a jelly (gel), a solution, or a suspension.

The topical composition can further include one or more inactive ingredients. The inactive ingredients include, for example, benzyl alcohol 1%; carbomer 1342; carbomer homopolymer type B; edetate disodium; medium chain triglycerides; mineral oil; purified water; sodium hydroxide; sodium thiosulfate; and sorbitan monooleate.

EXAMPLE 1

Synthesis of (Z)-3-(1-(4-(N-((4-methyl-piperazin-1-yl)-methylcarbonyl)-N-methyl-amino)-phenylamino)-1-phenyl-methylene]-6-methoxycarbonyl-2-indolinone (nintedanib)

Z)-3-(1-(4-(N-((4-methyl-piperazin-1-yl)-methylcarbonyl)-N-methyl-amino)-phenylamino)-1-phenyl-methylene]-6-methoxycarbonyl-2-indolinone is prepared by the method of synthesizing compound 473 described in PCT application publication no. WO 01/27081 A1.

EXAMPLE 2

Synthesis of 4-(4-(3-(4-Chloro-3-(trifluoromethyl)phenyl)ureido)-3-fluorophenoxy)-N-methylpicolinamide (regorafenib)

4-(4-(3-(4-Chloro-3-(trifluoromethyl)phenyl)ureido)-3-fluorophenoxy)-N-methylpicolinamide can be prepared by the method described in WO 2011/128261.

EXAMPLE 3 Synthesis of (5-Bromoquinoxalin-6-yl)-(4,5-dihydro-1H-imidazol-2-yl)-amine (brimonidine)

6-amino-5-bromoquinoxaline hydrobromide (10 g) is added to thiophosgene (3 ml) and distilled water (150 ml) while stirring. The mixture is reacted for two hours at room temperature and the resultant precipitate is filtered, washed with water, and dried to give 5-bromo-6-isothiocyanato-quinoxaline (3.6 g).

5-bromo-6-isothiocyanato-quinoxaline is dissolved in benzene (400 ml) and added drop-wise to a solution of ethylene diamine (15 g) in benzene (50 ml). The mixture is stirred for two hours, and an oil substrate separates as a lower layer. The upper benzene layer is discarded, and the oil is washed with diethyl ether and dissolved in methanol (500 ml). The methanol solution is refluxed to remove hydrogen sulfide. The methanol solution is then concentrated to a volume of about 100 ml, and a yellow solid then precipitates. The precipitate is collected by filtration and recrystallized from methanol to obtain (5-Bromo-quinoxalin-6-yl)-(4,5-dihydro-1H-imidazol-2-yl)-amine.

EXAMPLE 4

Synthesis of 6-tert-butyl-3-(4,5-dihydro-1H-imidazol-2-ylmethyl)-2,4-dimethylphenol (oxymetazoline)

6-tert-Butyl-3-(4,5-dihydro-1H-imidazol-2-ylmethyl)-2,4-dimethylphenol is prepared by reacting (4-tert-butyl-2,6-dimethyl-3-hydroxyphenyl)acetonitrile with ethylenediamine. The method is described in German patent no. DE 1117588.

EXAMPLE 5

Formulations

Vehicle cream: this formulation contains the following inactive ingredients: benzyl alcohol 1%; carbomer 1342; carbomer homopolymer type B; edetate disodium; medium chain triglycerides; mineral oil; purified water; sodium hydroxide; sodium thiosulfate; and sorbitan monooleate.

Vehicle gel: this formulation contains the following inactive ingredients: benzyl alcohol 1%; ascorbic acid; butylated hydroxyanisole; butylated hydroxytoluene; carbomer homopolymer type B; edetate disodium; hexylene glycol; poloxamer 407; polyethylene glycol 400; polysorbate 40; purified water; and tromethamine.

0.2% Nintedanib cream: this formulation contains 0.2% by weight nintedanib as the active ingredient and the following inactive ingredients: benzyl alcohol 1%; carbomer 1342; carbomer homopolymer type B; edetate disodium; medium chain triglycerides; mineral oil; purified water; sodium hydroxide; sodium thiosulfate; and sorbitan monooleate.

0.2% Nintedanib gel: this formulation contains 0.2% by weight nintedanib as the active ingredient and the following inactive ingredients: benzyl alcohol 1%; ascorbic acid; butylated hydroxyanisole; butylated hydroxytoluene; carbomer homopolymer type B; edetate disodium; hexylene glycol; poloxamer 407; polyethylene glycol 400; polysorbate 40; purified water; and tromethamine.

0.3% Brimonidine cream: this formulation contains 0.3% by weight brimonidine as the active ingredient and the following inactive ingredients: benzyl alcohol 1%; carbomer 1342; carbomer homopolymer type B; edetate disodium; medium chain triglycerides; mineral oil; purified water; sodium hydroxide; sodium thiosulfate; and sorbitan monooleate.

0.3% Brimonidine gel: this formulation contains 0.3% by weight brimonidine as the active ingredient and the following inactive ingredients: benzyl alcohol 1%; ascorbic acid; butylated hydroxyanisole; butylated hydroxytoluene; carbomer homopolymer type B; edetate disodium; hexylene glycol; poloxamer 407; polyethylene glycol 400; polysorbate 40; purified water; and tromethamine.

0.2% Nintedanib and 0.3% brimonidine cream: this formulation contains 0.2% by weight nintedanib and 0.3% brimonidine as the active ingredients and the following inactive ingredients: benzyl alcohol 1%; carbomer 1342; carbomer homopolymer type B; edetate disodium; medium chain triglycerides; mineral oil; purified water; sodium hydroxide; sodium thiosulfate; and sorbitan monooleate.

0.2% Nintedanib and 0.3% brimonidine gel: this formulation contains 0.2% by weight nintedanib and 0.3% brimonidine as active ingredients and the following inactive ingredients: benzyl alcohol 1%; ascorbic acid; butylated hydroxyanisole; butylated hydroxytoluene; carbomer homopolymer type B; edetate disodium; hexylene glycol; poloxamer 407; polyethylene glycol 400; polysorbate 40; purified water; and tromethamine.

0.1% Nintedanib and 0.15% brimonidine cream: this formulation contains 0.1% by weight nintedanib and 0.15% brimonidine as the active ingredients and the following inactive ingredients: benzyl alcohol 1%; carbomer 1342; carbomer homopolymer type B; edetate disodium; medium chain triglycerides; mineral oil; purified water; sodium hydroxide; sodium thiosulfate; and sorbitan monooleate.

0.1% Nintedanib and 0.15% brimonidine gel: this formulation contains 0.1% by weight nintedanib and 0.15% brimonidine as active ingredients and the following inactive ingredients: benzyl alcohol 1%; ascorbic acid; butylated hydroxyanisole; butylated hydroxytoluene; carbomer homopolymer type B; edetate disodium; hexylene glycol; poloxamer 407; polyethylene glycol 400; polysorbate 40; purified water; and tromethamine.

EXAMPLE 6

Balb/c LL-37 Mouse Model

In this example, LL-37 peptide is injected intradermally into Balb/c mice to induce inflammation and rosacea like erythema and telangiectasia on the skin. LL-37 is a key pathogenic factor in rosacea.

After two days of twice daily injection of LL-37, the mice are arranged into two groups. One group is treated with 0.2% nintedanib cream formulation topically at the shaved site and the other group is treated with a vehicle formulation. The treatment is TID ("ter in die," 3 times a day) for 2 weeks. The erythema and telangiectasia scores are measured on day 0, 1, 3, 7 and 14. The mice treated with the nintedanib cream show significantly less erythema and telangiectasia than the vehicle-treated mice. The result indicates that nintedanib is effective for treating rosacea.

EXAMPLE 7

Phymatous Rosacea

In this example, a nintedanib cream and its vehicle are tested in phymatous rosacea patients. A group of 10 patients are treated with the nintedanib cream and a second group of 10 patients are treated with the vehicle as control. The facial appearance of the patients is photographed and also imaged by using videomicroscope (VMS). The field of view of the VMS is 720 by 540 pixels. In the VMS images, the features of capillary blood vessels are evaluated and color space (L*a*b*) of facial skin is determined.

After 1 month of TID treatment, the nintedanib-treated group shows a 20-90% reduction of erythema and fibrosis in the lesion area comparing to the vehicle treated group by analyzing the phonographs and VMS images of the patients. For some patients, the reduction of erythema and fibrosis in the lesion area is 60-90%.

EXAMPLE 8

Erythema

Rosacea patients with moderate to severe persistent facial erythema are selected for treatment. The erythema is graded according to the Clinician Erythema Assessment (CEA) scale with photonumeric guide. It has a five-point scale: 0: clear skin with no signs of erythema; 1: almost clear, slight redness; 2: mild erythema, definite redness; 3: moderate erythema, marked redness; 4: severe erythema, fiery redness. Patients with CEA grade>3 are enrolled in the study.

The study is double-masked. There are 5 treatment groups for 5 cream formulations (vehicle, 0.2% nintedanib, 0.3% brimonidine, combo-1 [0.2% nintedanib and 0.3% brimonidine], and combo-2 [0.1% nintedanib and 0.15% brimonidine]) to be tested and each group will have about 20 patients. The patients are assigned to the groups in a way to make sure the base line average grade is similar among the groups. The formulations are dosed once daily for 4 weeks and the patients are further followed up for 8 weeks. The drug is administered by a physician on the first day of visit and then self-administered by the patient for the remaining 4 weeks. Patients are evaluated on day 1, week 2 and 4 during dosing. After the stop of dosing, patients are further followed up at week 8 and 12.

Endpoints:

The effect on erythema is evaluated by taking pictures of the face. The erythema is graded by an independent grader who does not know the treatments received. The tolerability of the formulations is also evaluated by assessing treatment related adverse events. The efficacy and tolerability data are analyzed by independent statisticians.

Results:

For the vehicle group, the erythema grade has no significant changes from the baseline at any of the visits. For the nintedanib group, the erythema grade does not change on day 1 but is reduced at week 1, 2 and 4 by about 1 grade. After the stop of treatment at week 4, the grade rebounded but still remains lower than the baseline at week 8 and 12. For the brimonidine group, the erythema grade reduced about 1 grade immediately after dosing on day 1. The reduction remains during the dosing at week 1-4. After stop of treatments, the grade rebounds and becomes slightly higher than baseline on week 8. It returns to the baseline at week 12. For the combo-1 group (0.2% nintedanib and 0.3% brimonidine cream), the day 1 drug effect is similar to that of the brimonidine group, with about 1 grade reduction. At week 1, 2 and 4, during dosing, the erythema grade reduction is more than either the nintedanib or brimonidine monotherapy group. The reduction reaches 2 grades at week 4. After the stop of dosing, the combo-1 group maintained significant reduction of erythema comparing to the monotherapy groups. The combo-2 (0.1% nintedanib and 0.15% brimonidine cream, half of combo-1) is still effective and shows erythema reductions comparable to the single drugs at twice the dose, and the effects are immediate and long lasting. This indicats that the combination of nintedanib and brimonidine can be effective to treat erythema at a low dose. The effects on erythema grade are summarized in Table 1 below.

No serious adverse effects and unacceptable adverse effects are observed in any of the groups.

TABLE 1

Average Erythema Grade for Each Group

|  | Vehicle | 0.2% Nintedanib | 0.3% Brimonidine | Combo-1 | Combo-2 |
| --- | --- | --- | --- | --- | --- |
| Day 1, baseline | 3.5 | 3.5 | 3.5 | 3.5 | 3.5 |
| Day 1, 2 h post | 3.5 | 3.5 | 2.5 | 2.5 | 2.5 |
| Week 1 | 3.5 | 2.5 | 2.5 | 2 | 2.5 |
| Week 2 | 3.5 | 2.5 | 2.5 | 2 | 2.5 |
| Week 4 | 3.5 | 2.5 | 2.5 | 1.5 | 2.5 |
| Week 8 | 3.5 | 2.8 | 3.7 | 2.5 | 3 |
| Week 12 | 3.5 | 3.1 | 3.5 | 3 | 3.2 |

EXAMPLE 9

Nintedanib Effectively Reduced Vascularity in Pterygium Patients

Pterygium is an ocular surface disease characterized with abnormal fibrovascular tissue growth. Hyperemia due to excess neovascularization is a prominent feature of the disease. Similar to rosacea, UV exposure is one of the important environmental pathogenic factors of the disease.

Nintedanib was formulated into an eye drop and tested in pterygium patients in a Phase 2a clinical trial to evaluate the safety and efficacy of nintedanib. The key efficacy endpoint is effects on pterygium vascularity.

The clinic trial was conducted in two stages. In stage 1, the safety, tolerability and pharmacokinetics were evaluated in a single dose escalating study. Three dose cohorts with 8 patients in each were evaluated. Cohort 1 began at the lowest concentration of 0.02% nintedanib (weight percent based on the total weight of the eye drop), followed by an increasing dose to 0.05% for Cohort 2 and then to 0.2% for Cohort 3. No safety issues were found at all doses so the highest dose of 0.2% is chosen for stage 2.

In stage 2, the safety, tolerability and efficacy of the 0.2% formulation were evaluated in a randomized, double-masked, vehicle-controlled, parallel study with 28 days TID repeat ocular dosing of vehicle and 0.2% nintedanib. The patients were further followed up by 20 weeks of post-dosing observation. Ophthalmic and physical examinations were performed at screening, Day 1 and Week 2, 4, 8, 16, and 24. External photograph of the pterygium eye was taken using a digital camera and the pterygium vascularity was graded from these images at an independent image reading center. The primary objective is to evaluate ocular and systemic safety of nintedanib in pterygium patients that have moderate to severe pterygium vascularity. The secondary objective is to assess whether the formulation is efficacious in reducing pterygium vascularity.

A total of 50 patients were enrolled and randomized in a 1:1 treatment allocation to receive either nintedanib or vehicle. The final analysis was performed after study completion. The O'Brien-Fleming group-sequential method was used for a multiple-comparison adjustment of p-values for efficacy. For the final analysis, a 2-sided test with p-value≤0.048 is considered statistically significant for all between and within treatment comparisons.

The safety and tolerability of the nintedanib formulation is excellent with no serious adverse events and some acceptable adverse events commonly associated with eye drops. The effect on pterygium vascularity is highly significant by Week 2 and the effects maintained through Week 16, 2 months after dosing had stopped. The results are summarized in Table 2 that shows the mean grade difference and the change from baseline difference between drug and vehicle groups.

This example demonstrated the potent effect of nintedanib on abnormal vascularity, a feature also presents in rosacea.

TABLE 2

Nintedanib Effectively Reduced Vascularity in Pterygium Patients

| | Nintedanib vs vehicle differences | | | |
| --- | --- | --- | --- | --- |
| | Mean grade | | Mean change from baseline | |
| | Difference | P value | Difference | P value |
| Day 1 (baseline) | −0.15 | 0.492 | NA | NA |
| Week 2 | −0.87 | 0.001 | −0.72 | 0.0000 |
| Week 4 (end of dosing) | −0.91 | 0.0002 | −0.76 | 0.0004 |
| Week 8 | −0.53 | 0.0143 | −0.41 | 0.0084 |
| Week 16 | −0.7 | 0.0017 | −0.59 | 0.0006 |
| Week 24 (end of study) | −0.31 | 0.1153 | −0.17 | 0.2661 |

REFERENCES

Abokwidir and Feldman. Rosacea Management. Skin Appendage Disord. 2016 September; 2(1-2):26-34.

Gomaa A H, Yaar M, Eyada M M, Bhawan J. Lymphangiogenesis and angiogenesis in non-phymatous rosacea. J Cutan Pathol. 2007 October; 34(10):748-53.

Holmes A D and Steinhoff M. Integrative concepts of rosacea pathophysiology, clinical presentation and new therapeutics. Exp Dermatol. 2016 Jul. 4, 1-9.

Nijnik A, Pistolic J, Cho P, Filewod N C, Falsafi R, Ramin A, Harder K W, Hancock R E. The role of the Src family kinase Lyn in the immunomodulatory activities of cathelicidin peptide LL-37 on monocytic cells. J Leukoc Biol. 2012 April; 91(4):599-607.

Schwab V D, Sulk M, Seeliger S, Nowak P, Aubert J, Mess C, Rivier M, Carlavan I, Rossio P, Metze D, Buddenkotte J, Cevikbas F, Voegel J J, Steinhoff M. Neurovascular and neuroimmune aspects in the pathophysiology of rosacea. J Investig Dermatol Symp Proc. 2011 December; 15 (1):53-62.

Woo Y R, Lim J H, Cho D H, Park H J. Rosacea: Molecular Mechanisms and Management of a Chronic Cutaneous Inflammatory Condition. Int J Mol Sci. 2016 Sep. 15; 17(9). pii: E1562.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method for treating rosacea for a patient comprising:
    inhibiting a Vascular Endothelial Growth Factor Receptor of the patient;
    inhibiting a Fibroblast Growth Factor Receptor of the patient, wherein inhibiting the Vascular Endothelial Growth Factor Receptor and the Fibroblast Growth Factor Receptor comprises administering 0.1% of nintedanib; and
    activating an adrenergic receptor by administering 0.15% of brimonidine to the patient as a combination therapy with nintedanib.

2. The method of claim 1, wherein the Vascular Endothelial Growth Factor Receptor is Vascular Endothelial Growth Factor Receptor 1, 2, or 3, and the Fibroblast Growth Factor Receptor is Fibroblast Growth Factor Receptor 2.

3. The method of claim 1, wherein nintedanib or regorafenib reduces abnormal dermal blood vessel angiogenesis, leakage, density, redness, abnormal lymph angiogenesis or inflammation in the patient.

4. The method of claim 1, wherein nintedanib or regorafenib reduces abnormal neurovascular regulation in the patient by attenuating signals of Vascular Endothelial Growth Factor and Fibroblast Growth Factor.

5. The method of claim 1, wherein nintedanib inhibits Lyn kinase and attenuates LL-37 mediated inflammation in the patient.

* * * * *